United States Patent
Liu et al.

(10) Patent No.: US 11,820,724 B2
(45) Date of Patent: Nov. 21, 2023

(54) METHOD FOR PREPARING 2-ETHYL-4-FLUORO-1-NITROBENZENE

(71) Applicants: ACCELA CHEMBIO CO., LTD., Shanghai (CN); QIDONG ACCELA CHEMBIO CO., LTD., Jiangsu (CN)

(72) Inventors: Yang Liu, Shanghai (CN); Duoqing Xue, Shanghai (CN); Yong Wu, Shanghai (CN); Lihuang Chen, Shanghai (CN); Lianhua Zhai, Shanghai (CN)

(73) Assignee: ACCELA CHEMBIO CO., LTD., Shanghai (CN)

( * ) Notice: Subject to any disclaimer, the term of this patent is extended or adjusted under 35 U.S.C. 154(b) by 426 days.

(21) Appl. No.: 17/296,544

(22) PCT Filed: Sep. 10, 2020

(86) PCT No.: PCT/CN2020/114309
§ 371 (c)(1),
(2) Date: May 24, 2021

(87) PCT Pub. No.: WO2021/082752
PCT Pub. Date: May 6, 2021

(65) Prior Publication Data
US 2022/0024850 A1    Jan. 27, 2022

(30) Foreign Application Priority Data
Nov. 1, 2019 (CN) .......... 201911060770.4

(51) Int. Cl.
*C07C 201/08* (2006.01)
*C07C 201/12* (2006.01)

(52) U.S. Cl.
CPC .......... *C07C 201/08* (2013.01); *C07C 201/12* (2013.01)

(58) Field of Classification Search
CPC ... C07C 201/08; C07C 201/12; C07C 205/12; C07C 205/26; C07C 205/11; C07C 205/06; C07C 205/19
See application file for complete search history.

(56) References Cited

U.S. PATENT DOCUMENTS

2002/0037875 A1    3/2002    Banville et al.

FOREIGN PATENT DOCUMENTS

| CN | 106687457 A | 5/2017 |
| CN | 110498744 A | 11/2019 |
| CN | 110746307 A | 2/2020 |

OTHER PUBLICATIONS

International Search Report and Written Opinion in the international application No. PCT/CN2020/114309, dated Dec. 9, 2020 (unofficial translation of ISR only; pp. 1-3).

*Primary Examiner* — Jafar F Parsa
(74) *Attorney, Agent, or Firm* — Perkins Coie LLP; Han-Wei Chen

(57) ABSTRACT

The present disclosure provides a method for preparing 2-ethyl-4-fluoro-1-nitrobenzene, including: (1) nitrifying 3-fluoroacetophenone with a nitration reagent, to obtain 1-(5-fluoro-2-nitrophenyl)ethanone; (2) reducing 1-(5-fluoro-2-nitrophenyl)ethanone with a reducing agent, to obtain 4-fluoro-2-(1-hydroxyethyl)-1-nitrobenzene; (3) iodinating 4-fluoro-2-(1-hydroxyethyl)-1-nitrobenzene, to obtain 4-fluoro-2-(1-iodoethyl)-1-nitrobenzene; and (4) reducing 4-fluoro-2-(1-iodoethyl)-1-nitrobenzene with a reducing agent, to obtain 2-ethyl-4-fluoro-1-nitrobenzene.

20 Claims, No Drawings

METHOD FOR PREPARING 2-ETHYL-4-FLUORO-1-NITROBENZENE

CROSS REFERENCE TO RELATED APPLICATION

This application claims the priority of Chinese Patent Application No. 201911060770.4, entitled "Method for preparing 2-ethyl-4-fluoro-1-nitrobenzene" filed with the China National Intellectual Property Administration on Nov. 1, 2019, which is incorporated herein by reference in its entirety.

TECHNICAL FIELD

The present disclosure relates to the technical field of organic synthesis, and in particular to a method for preparing 2-ethyl-4-fluoro-1-nitrobenzene.

BACKGROUND ART

4-Fluoronitrobenzene compounds are crucial intermediates in the preparation of medicine, pesticide, dye and photosensitive material, which are widely used in the synthesis of antibacterial western medicine, highly potent herbicide and the like. Among others, 2-ethyl-4-fluoro-1-nitrobenzene is an important component for 4-fluoronitrobenzene compounds, and it is conventionally synthesized by using 5-fluoro-2-nitroaniline as a raw material and subjecting it to diazotization and Negishi coupling reaction in sequence. However, in terms of this synthesis route, the reagent used is high in cost, the product yield is low and the safety is relatively poor. More particularly, in terms of the Negishi coupling reaction, organiczinc reagents and halogenated aromatics undergo a coupling reaction in the presence of nickel or palladium complex catalyst, in which the catalyst is expensive; there is obvious accumulation and exothermic phenomenon during the reaction, which exists dangerousness to some extent, and thus it has very high requirements for the reaction equipment and the treatment capacity of operator; moreover, the final product is difficult to purify. In view of this, the process only is suitable for small-scale laboratory preparation regardless of cost, and cannot realize kilogram scale amplification, and it is more difficult to realize industrial and scale-up production.

Therefore, a research emphasis in the art is to develop a method for preparing 2-ethyl-4-fluoro-1-nitrobenzene, with high product yield, high product purity, low cost, and safe synthesis route, so as to realize the industrial and scale-up production of 2-ethyl-4-fluoro-1-nitrobenzene.

SUMMARY

In order to achieve the above objective, the present disclosure provides the following technical solutions:

The present disclosure provides a method for preparing 2-ethyl-4-fluoro-1-nitrobenzene, comprising, (1) nitrifying 3-fluoroacetophenone with a nitration reagent, to obtain 1-(5-fluoro-2-nitrophenyl)ethanone;

(2) reducing 1-(5-fluoro-2-nitrophenyl)ethanone obtained in step (1) with a reducing agent, to obtain 4-fluoro-2-(1-hydroxyethyl)-1-nitrobenzene;

(3) iodinating 4-fluoro-2-(1-hydroxyethyl)-1-nitrobenzene obtained in step (2), to obtain 4-fluoro-2-(1-iodoethyl)-1-nitrobenzene; and (4) reducing 4-fluoro-2-(1-iodoethyl)-1-nitrobenzene obtained in step (3) with a reducing agent, to obtain 2-ethyl-4-fluoro-1-nitrobenzene.

The reaction route of the preparation method is shown in Formula 1:

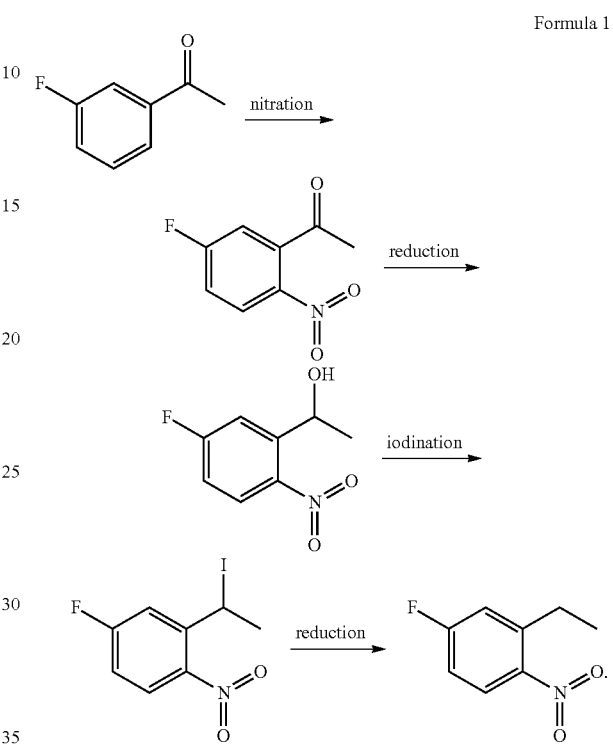

Formula 1

In the method for preparing 2-ethyl-4-fluoro-1-nitrobenzene according to the present disclosure, 3-fluoroacetophenone is used as a raw material and subjected to nitration, reduction, iodination and reduction in sequence, to obtain the target product 2-ethyl-4-fluoro-1-nitrobenzene. By means of a special design of the above route, the preparation method enables the process safety to be significantly improved, and makes the preparation condition more mild without involving dangerousness processes such as high temperature, high pressure, and a large amount of heat release, being suitable for industrial and scale-up production. Furthermore, the raw material used in the preparation method has a low cost, which greatly reduces the production cost of 2-ethyl-4-fluoro-1-nitrobenzene. More importantly, by means of a optimal design of the above route, the preparation method according to the present disclosure enables the utilization rate of the raw material to be improved, and makes the product easy to be separated and purified, making the product yield more than 60% and the purity not less than 98%. Therefore, the preparation method according to the present disclosure is suitable for industrial and scale-up production in terms of the process safety, cost, the utilization rate of raw material, the product purity and the like.

In some embodiments, the nitration reagent in step (1) is fuming nitric acid.

In some embodiments, a mass ratio of fuming nitric acid to 3-fluoroacetophenone is in the range of (5.0-8.0):1, such as 5.1:1, 5.3:1, 5.5:1, 5.7:1, 5.9:1, 6:1, 6.2:1, 6.4:1, 6.6:1, 6.8:1, 7:1, 7.2:1, 7.4:1, 7.5:1, 7.7:1 or 7.9:1.

In some embodiments, the nitration in step (1) is performed at a temperature of −15° C. to −5° C., such as −14° C., −13° C., −12° C., −11° C., −10° C., −9° C., −8° C., −7° C. or −6° C.

In some embodiments, the nitration in step (1) is performed for 2-5 h, such as 2.2 h, 2.5 h, 2.8 h, 3 h, 3.3 h, 3.5 h, 3.8 h, 4 h, 4.3 h, 4.5 h or 4.8 h.

In some embodiments, step (1) further comprises subjecting a nitrified solution obtained after nitrifying 3-fluoroacetophenone to a post-treatment.

In some embodiments, the post-treatment comprises: quenching the nitrified solution with ice water, then stirring and filtering to obtain a solid phase, and collecting the solid phase, to obtain 1-(5-fluoro-2-nitrophenyl)ethanone.

In some embodiments, the stirring is performed at a temperature of 0° C. to 5° C., such as 1° C., 2° C., 3° C. or 4° C.

In some embodiments, the stirring is performed for 30-90 min, such as 35 min, 40 min, 45 min, 50 min, 55 min, 60 min, 65 min, 70 min, 75 min, 80 min or 85 min.

In some embodiments, the reducing agent in step (2) is sodium borohydride.

In some embodiments, a molar ratio of sodium borohydride to 1-(5-fluoro-2-nitrophenyl)ethanone is in the range of (0.3-2.0):1, such as 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1 or 1.9:1.

In some embodiments, the reducing in step (2) is performed at a temperature of 15° C. to 25° C., such as 16° C., 17° C., 18° C., 19° C., 20° C., 21° C., 22° C., 23° C. or 24° C.

In some embodiments, the reducing in step (2) is performed for 1-3 h, such as 1.2 h, 1.5 h, 1.8 h, 2 h, 2.3 h, 2.5 h, 2.7 h or 2.9 h.

In some embodiments, the reducing in step (2) is performed in the presence of a solvent.

In some embodiments, the solvent is tetrahydrofuran and/or absolute methanol.

In some embodiments, the solvent is used in an amount of 0.8-1.5 L, such as 0.9 L, 1 L, 1.1 L, 1.2 L, 1.3 L or 1.4 L, based on 1 mol of 1-(5-fluoro-2-nitrophenyl)ethanone.

In some embodiments, the step (2) further comprises subjecting a reduced solution obtained after reducing 1-(5-fluoro-2-nitrophenyl)ethanone to a post-treatment.

In some embodiments, the post-treatment comprises: quenching the reduced solution with an acid, then extracting the reduced solution to obtain an organic phase, and collecting the organic phase, then concentrating and purifying the organic phase, to obtain 4-fluoro-2-(1-hydroxyethyl)-1-nitrobenzene.

In some embodiments, the acid is hydrochloric acid with a concentration of 0.4-1 N, such as 0.4 N, 0.5 N, 0.6 N, 0.7 N, 0.8 N, 0.9 N or 0.95 N.

According to the present disclosure, the term "0.4-1 N" as used herein means that a equivalent concentration is 0.4-1, i.e. the gram equivalent amount of solute in 1 L solution is 0.4-1. The same description hereinafter has the same meaning.

In some embodiments, the solvent used in the extracting is ethyl acetate.

In some embodiments, the iodination in step (3) is performed by the following iodination scheme I or iodination scheme II.

The iodination scheme I comprises: mixing triphenylphosphine and imidazole to obtain a mixture, adding an iodine source into the mixture under a protective atmosphere, and subjecting the reactants to a first reaction, to obtain a reaction system; then adding 4-fluoro-2-(1-hydroxyethyl)-1-nitrobenzene into the reaction system, and subjecting the resulting mixture to a second reaction, to obtain 4-fluoro-2-(1-iodoethyl)-1-nitrobenzene.

The iodination scheme II comprises: adding methanesulfonyl chloride into 4-fluoro-2-(1-hydroxyethyl)-1-nitrobenzene, and subjecting the resulting mixture to a methylsulfonylation reaction, to obtain 1-(5-fluoro-2-nitrobenzene)ethylmethanesulfonate; then iodinating 1-(5-fluoro-2-nitrobenzene)ethylmethanesulfonate with an iodine source, to obtain 4-fluoro-2-(1-iodoethyl)-1-nitrobenzene. The reaction route is shown in Formula 2:

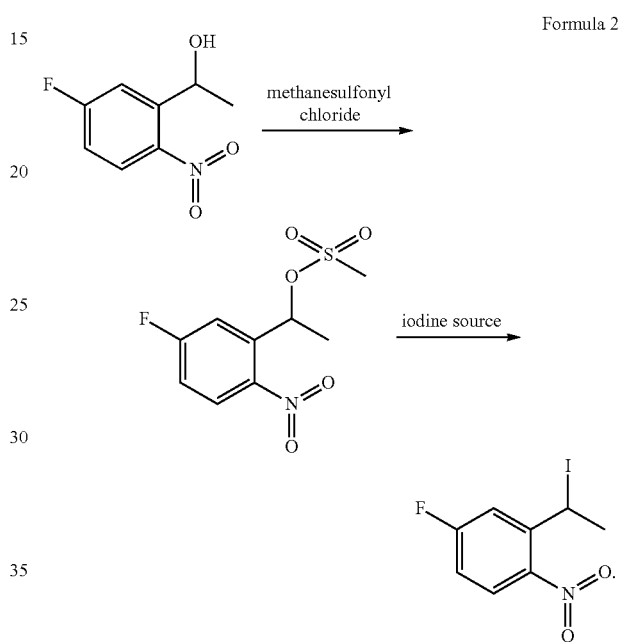

Formula 2

In some embodiments, the iodine source in the iodination scheme I is iodine.

In some embodiments, a molar ratio of iodine, triphenylphosphine and imidazole is in the range of (0.95-1.05):(0.95-1.05):1, such as 0.95:0.95:1, 1:0.95:1, 1.05:0.95:1, 0.95:1:1, 1:1:1, 1.05:1:1, 0.95:1.05:1, 1:1.05:1 or 1.05:1.05:1.

In some embodiments, a molar ratio of iodine to 4-fluoro-2-(1-hydroxyethyl)-1-nitrobenzene is in the range of (1.3-2.5):1, such as 1.4:1, 1.5:1, 1.6:1, 1.7:1, 1.8:1, 1.9:1, 2:1, 2.1:1, 2.2:1, 2.3:1 or 2.4:1, preferably (1.4-1.6):1.

In some embodiments, the reaction in the iodination scheme I is performed in the presence of a solvent.

In some embodiments, the solvent is dichloromethane.

In some embodiments, the solvent is used in an amount of 0.8-1.5 L, such as 0.9 L, 1 L, 1.1 L, 1.2 L, 1.3 L or 1.4 L, based on 1 mol of triphenylphosphine.

In some embodiments, the first reaction in the iodination scheme I is performed at a temperature of −5° C. to 0° C., such as −4.5° C., −4° C., −3.5° C., −3° C., −2.5° C., −2° C., −1.5° C., −1° C. or −0.5° C.

In some embodiments, the first reaction in the iodination scheme I is performed for 20-40 min, such as 21 min, 23 min, 25 min, 28 min, 30 min, 32 min, 35 min, 37 min or 39 min.

In some embodiments, the second reaction in the iodination scheme II is performed at a temperature of −5° C. to 5° C., such as −4° C., −3° C., −2° C., −1° C., 0° C., 1° C., 2° C., 3° C. or 4° C.

In some embodiments, the second reaction in the iodination scheme II is performed for 2-5 h, such as 2.2 h, 2.5 h, 2.8 h, 3 h, 3.2 h, 3.5 h, 3.8 h, 4 h, 4.2 h, 4.5 h, 4.7 h or 4.9 h.

In some embodiments, the iodination scheme I further comprises subjecting an iodination solution I to a post-treatment.

In some embodiments, the post-treatment comprises: quenching the iodination solution I with an acid, then separating liquid to obtain an organic phase, and collecting the organic phase, purifying and concentrating the organic phase, to obtain 4-fluoro-2-(1-iodoethyl)-1-nitrobenzene.

In some embodiments, the acid is hydrochloric acid with a concentration of 0.4-1 N, such as 0.4 N, 0.5 N, 0.6 N, 0.7 N, 0.8 N, 0.9 N or 0.95 N.

In some embodiments, a molar ratio of 4-fluoro-2-(1-hydroxyethyl)-1-nitrobenzene to methanesulfonyl chloride in the iodination scheme II is in the range of 1:(1.05-2.0), such as 1:1.06, 1:1.08, 1:1.1, 1:1.15, 1:1.2, 1:1.25, 1:1.3, 1:1.35, 1:1.4, 1:1.45, 1:1.5, 1:1.55, 1:1.6, 1:1.65, 1:1.7, 1:1.75, 1:1.8, 1:1.85, 1:1.9 or 1:1.95.

In some embodiments, in the iodination scheme II methanesulfonyl chloride is added by dropwise adding.

In some embodiments, the dropwise adding is performed at a temperature of 0° C. to 10° C., such as 1° C., 2° C., 3° C., 4° C., 5° C., 6° C., 7° C., 8° C., 9° C. or 9.5° C.

In some embodiments, the raw materials used in the methylsulfonylation reaction in the iodination scheme II further comprise an acid-binding agent.

In some embodiments, the acid-binding agent is one selected from the group consisting of triethylamine, pyridine, sodium carbonate and sodium bicarbonate.

In some embodiments, a molar ratio of the acid-binding agent to methanesulfonyl chloride is in the range of (0.9-1.1):1, such as 0.91:1, 0.93:1, 0.95:1, 0.97:1, 0.99:1, 1:1, 1.02:1, 1.04:1, 1.06:1, 1.08:1 or 1.09:1.

In some embodiments, the methylsulfonylation reaction in the iodination scheme II is performed in the presence of a solvent.

In some embodiments, the solvent is dichloromethane.

In some embodiments, the solvent is used in an amount of 1.5-2.5 L, such as 1.6 L, 1.7 L, 1.8 L, 1.9 L, 2 L, 2.1 L, 2.2 L, 2.3 L, 2.4 L or 2.45 L, based on 1 mol of 4-fluoro-2-(1-hydroxyethyl)-1-nitrobenzene.

In some embodiments, the methylsulfonylation reaction in the iodination scheme II is performed at a temperature of 20° C. to 30° C., such as 21° C., 22° C., 23° C., 24° C., 25° C., 26° C., 27° C., 28° C. or 29° C.

In some embodiments, the methylsulfonylation reaction in the iodination scheme II is performed for 4-6 h, such as 4.1 h, 4.3 h, 4.5 h, 4.7 h, 4.9 h, 5 h, 5.2 h, 5.4 h, 5.5 h, 5.7 h or 5.9 h.

In some embodiments, the iodination scheme II further comprises subjecting a reaction solution obtained after the methylsulfonylation reaction to a post-treatment.

In some embodiments, the post-treatment comprises: quenching the reaction solution with an acid, then extracting the reaction solution to obtain an organic phase, and collecting the organic phase, then washing, concentrating and drying the organic phase, to obtain 1-(5-fluoro-2-nitrobenzene)ethylmethanesulfonate, wherein the acid is hydrochloric acid with a concentration of 0.4-1 N, such as 0.4 N, 0.5 N, 0.6 N, 0.7 N, 0.8 N, 0.9 N or 0.95 N.

In some embodiments, the iodine source in the iodination scheme II is sodium iodide.

In some embodiments, a molar ratio of sodium iodide to 1-(5-fluoro-2-nitrobenzene)ethylmethanesulfonate in the iodination scheme II is in the range of (1.0-3.0):1, such as 1.1:1, 1.2:1, 1.3:1, 1.4:1, 1.5:1, 1.6:1, 1.7:1, 1.8:1, 1.9:1, 2:1, 2.2:1, 2.3:1, 2.4:1, 2.5:1, 2.6:1, 2.7:1, 2.8:1 or 2.9:1.

In some embodiments, the iodinating in the iodination scheme II is performed in the presence of a solvent.

In some embodiments, the solvent is acetone.

In some embodiments, the solvent is used in an amount of 1.8-2.5 L, such as 1.85 L, 1.9 L, 2 L, 2.1 L, 2.2 L, 2.3 L, 2.4 L or 2.45 L, based on 1 mol of 1-(5-fluoro-2-nitrobenzene)ethylmethanesulfonate.

In some embodiments, the iodinating in the iodination scheme II is performed at a temperature of 35° C. to 40° C., such as 35.5° C., 36° C., 36.5° C., 37° C., 37.5° C., 38° C., 38.5° C., 39° C. or 39.5° C.

In some embodiments, the iodinating in the iodination scheme II is performed for 6-16 h, such as 6.5 h, 7 h, 7.5 h, 8 h, 8.5 h, 9 h, 9.5 h, 10 h, 10.5 h, 11 h, 11.5 h, 12 h, 12.5 h, 13 h, 13.5 h, 14 h, 14.5 h, 15 h or 15.5 h.

In some embodiments, the reducing agent used in step (4) is sodium borohydride.

In some embodiments, a molar ratio of sodium borohydride to 4-fluoro-2-(1-iodoethyl)-1-nitrobenzene is in the range of (1.05-1.5):1, such as 1.06:1, 1.08:1, 1:1, 1.12:1, 1.15:1, 1.17:1, 1.2:1, 1.23:1, 1.25:1, 1.28:1, 1.3:1, 1.33:1, 1.35:1, 1.38:1, 1.4:1, 1.42:1, 1.45:1, 1.47:1 or 1.49:1.

In some embodiments, the reduction in step (4) is performed in the presence of a solvent.

In some embodiments, the solvent is N,N-dimethylformamide.

In some embodiments, the solvent is used in an amount of 1-2 L, such as 1.1 L, 1.2 L, 1.3 L, 1.4 L, 1.5 L, 1.6 L, 1.7 L, 1.8 L or 1.9 L, based on 1 mol of 4-fluoro-2-(1-iodoethyl)-1-nitrobenzene.

In some embodiments, the reduction in step (4) is performed at a temperature of 25° C. to 30° C., such as 25.5° C., 26° C., 26.5° C., 27° C., 27.5° C., 28° C., 28.5° C., 29° C. or 29.5° C.

In some embodiments, the reduction in step (4) is performed for 2-4 h, such as 2.2 h, 2.5 h, 2.7 h, 2.9 h, 3 h, 3.2 h, 3.5 h, 3.7 h or 3.9 h.

In some embodiments, the step (4) further comprises subjecting a reduced solution obtained after reducing 4-fluoro-2-(1-iodoethyl)-1-nitrobenzene to a post-treatment.

In some embodiments, the post-treatment comprises: quenching the reduced solution with an acid, then extracting the reduced solution with an organic solvent, then washing, concentrating and rectifying the extracted product, to obtain 2-ethyl-4-fluoro-1-nitrobenzene, wherein the acid is hydrochloric acid with a concentration of 0.4-1 N, such as 0.4 N, 0.5 N, 0.6 N, 0.7 N, 0.8 N, 0.9 N or 0.95 N.

In some embodiments, the organic solvent is isopropyl ether.

In some embodiments, fractions produced during the rectification is collected at a temperature of 64° C. to 66° C., such as 64.2° C., 64.5° C., 64.8° C., 65° C., 65.3° C., 65.5° C., 65.7° C. or 65.9° C., and a pressure of 0.1 Torr.

In some embodiments, the preparation method according to the present disclosure comprises the following steps:

(1) dropwise adding 3-fluoroacetophenone into fuming nitric acid at a temperature of −15° C. to −5° C., after the completion of the dropwise adding, nitrating the reactant at a temperature of −15° C. to −5° C. for 2-5 h, quenching the resulting reaction solution with ice water, then stirring at a temperature of 0-5° C. for 30-90 min and filtering the resulting reaction solution to obtain a solid phase, and collecting the solid phase, to obtain 1-(5-fluoro-2-nitrophenyl)ethanone, wherein a mass ratio of the fuming nitric acid to 3-fluoroacetophenone is in the range of (5.0-8.0):1;

(2) mixing 1-(5-fluoro-2-nitrophenyl)ethanone obtained in step (1) with a solvent to obtain a mixture, then adding sodium borohydride into the mixture, reducing the reactant at a temperature of 15-25° C. for 1-3 h, quenching the resulting reaction solution with an acid, then extracting the resulting reaction solution to give an organic phase, and collecting the organic phase, then concentrating and purifying the organic phase, to obtain 4-fluoro-2-(1-hydroxyethyl)-1-nitrobenzene, wherein a molar ratio of sodium borohydride to 1-(5-fluoro-2-nitrophenyl)ethanone is in the range of (0.3-2.0) 1;

(3) iodating 4-fluoro-2-(1-hydroxyethyl)-1-nitrobenzene obtained in step (2), wherein the iodating is performed by the following iodination scheme I or iodination scheme II, wherein, [84] the iodination scheme I comprises: mixing triphenylphosphine, imidazole and a solvent to obtain a mixture, then adding iodine into the mixture at a temperature of −5-0° C. under a protective atmosphere, after the completion of the adding, reacting the reactants at a temperature of −5-0° C. for 20-40 min to obtain a reaction system, then dropwise adding 4-fluoro-2-(1-hydroxyethyl)-1-nitrobenzene into the reaction system, after the completion of the dropwise adding, reacting the resulting mixture at a temperature of −5-5° C. for 2-5 h, quenching the resulting reaction solution with an acid, then separating liquid to give an organic phase, and collecting the organic phase, then purifying and concentrating the organic phase, to obtain 4-fluoro-2-(1-iodoethyl)-1-nitrobenzene, wherein a molar ratio of iodine, triphenylphosphine and imidazole is in the range of (0.95-1.05):(0.95-1.05):1, and a molar ratio of iodine to 4-fluoro-2-(1-hydroxyethyl)-1-nitrobenzene is in the range of (1.3-2.5):1; and [85] the iodination scheme II comprises: mixing 4-fluoro-2-(1-hydroxyethyl)-1-nitrobenzene, an acid-binding agent and a solvent to obtain a mixture, then dropwise adding methanesulfonyl chloride into the mixture at a temperature of 0-10° C., after the completion of the dropwise adding, subjecting the reactant to a methylsulfonylation reaction at a temperature of 20-30° C. for 4-6 h, quenching the resulting reaction solution with an acid, then extracting the resulting reaction solution, to obtain 1-(5-fluoro-2-nitrobenzene)ethylmethanesulfonate; iodating 1-(5-fluoro-2-nitrobenzene)ethylmethanesulfonate with sodium iodide in a solvent at a temperature of 35-40° C. for 6-16 h, then collecting, extracting and washing the resulting reaction solution, to obtain 4-fluoro-2-(1-iodoethyl)-1-nitrobenzene, wherein a molar ratio of 4-fluoro-2-(1-hydroxyethyl)-1-nitrobenzene to methanesulfonyl chloride is in the range of 1:(1.05-2.0), and a molar ratio of sodium iodide to 1-(5-fluoro-2-nitrobenzene)ethylmethanesulfonate is in the range of (1.0-3.0):1; and (4) mixing 4-fluoro-2-(1-iodoethyl)-1-nitrobenzene obtained in step (3) with a solvent to obtain a mixture, then adding sodium borohydride into the mixture, reducing the reactant at a temperature of 25-30° C. for 2-4 h, quenching the resulting reaction solution with an acid, then purifying the resulting reaction solution with an organic solvent, and washing, concentrating, rectifying the purified reaction solution to give fractions, and collecting the fractions at a temperature of 64-66° C. and a pressure of 0.1 Torr, to obtain 2-ethyl-4-fluoro-1-nitrobenzene, wherein a molar ratio of sodium borohydride to 4-fluoro-2-(1-iodoethyl)-1-nitrobenzene is in the range of (1.05-1.5):1.

Compared with the prior art, the present disclosure has the following beneficial effects:

In the method for preparing 2-ethyl-4-fluoro-1-nitrobenzene according to the present disclosure, 3-fluoroacetophenone is used as a raw material and subjected to nitration, reduction, iodination, and reduction in sequence, to obtain the target product 2-ethyl-4-fluoro-1-nitrobenzene. With the method, it is possible to make the product yield more than 60% and the product purity not less than 98%. In the present disclosure, by means of the design of the synthesis route, the preparation method not only enables the yield and purity of the 2-ethyl-4-fluoro-1-nitrobenzene to be significantly improved, but also makes the preparation condition more mild, the process safety high, the raw material cost low, being suitable for industrial and scale-up production, and having widely application prospects.

DETAILED DESCRIPTION OF THE EMBODIMENTS

The technical solutions provided by the present disclosure will be further illustrated below with reference to the embodiments. It should be understood that the embodiments are only to help understand the present disclosure, but should not be regarded as specific limiting the protection scope of the present disclosure.

All the experiment reagents used in the examples below in the present disclosure were commercially available. The reaction end point and the product purity were measured by high performance liquid chromatography (HPLC) (HPLC, Agilent Agilent 1260) according to internal standard method, and the specific measure was performed under the following conditions: C18 chromatographic column (4.6 mm×100 mm×2.7 m); mobile phase A: 0.05% of trifluoroacetic acid aqueous solution; mobile phase B: 0.05% of trifluoroacetic acid-acetonitrile solution; a mobile phase flow rate: 1.2 mL/min; injection volume: 1 L; a detection wavelength: 214 nm; a column temperature: 35° C. The yield was mass yield.

Example 1

The present example provided a method for preparing 2-ethyl-4-fluoro-1-nitrobenzene, which was performed according to the following procedure:

(1) 2330 g of fuming nitric acid was added into a reaction bulb, and 362 g 3-fluoroacetophenone was added dropwise into the reaction bulb at −10° C. After the completion of the dropwise adding, the reactants were reacted at −8° C. for 3 h while stirring, obtaining a reaction solution. Then the reaction solution was sampled and measured with HPLC to determine whether the reaction reached the end point. After reaching the end point, the reaction solution was quenched by slowly pouring into ice water, stirred at 3° C. for 1 h and filtered, obtaining a solid phase. The solid phase was collected and washed with water, and then the washed solid phase was dried by vacuum, obtaining 360 g of 1-(5-fluoro-2-nitrophenyl)ethanone. The yield was 75% and the purity was 98.5%.

The product 1-(5-fluoro-2-nitrophenyl)ethanone was tested, and the results were as follows: $^1$H-NMR (300 MHz, CDCl$_3$): δ 8.25 (m, 1H), 7.25 (m, 1H), 7.10 (d, 1H), 2.57 (s, 3H).

(2) 360 g of 1-(5-fluoro-2-nitrophenyl)ethanone obtained in step (1), 1.6 L of tetrahydrofuran and 0.5 L of absolute methanol were added into a reaction bulb to obtain a mixture, and 75 g of sodium borohydride was added into the mixture in batches at 20° C. After the completion of the adding, the reactants were reacted at 20° C. for 2 h while stirring, obtaining a reaction solution. Then the reaction solution was sampled and measured with HPLC to determine whether the reaction reached the end point. After reaching the end point, 0.5 N of hydrochloric acid and ethyl acetate were added thereto, and the resulting mixture was stirred, stood for a period, and separated liquid, obtaining an aqueous phase and an organic phases. The organic phase was collected, and the aqueous phase was extracted twice with ethyl acetate. The organic phase was combined and washed with saturated salt solution, and concentrated until no fraction came out. Anhydrous sodium sulfate, activated carbon and dichloromethane were added into the concentrated product to obtain a mixture, and the mixture was stirred for 2 h and filtered, obtaining a filter cake. The filter cake was washed with dichloromethane, and the resulting filter liquor was combined, concentrated and replaced twice with dichloromethane, obtaining 360 g of 4-fluoro-2-(1-hydroxyethyl)-1-nitrobenzene. The yield was 99%, and the purity was 99.0%.

The product 4-fluoro-2-(1-hydroxyethyl)-1-nitrobenzene was tested, and the results were as follows: $^1$H-NMR (300 MHz, CDCl$_3$): δ 8.05 (m, 1H), 7.60 (dd, 1H), 7.11 (m, 1H), 5.52 (q, 1H), 2.35 (br, 1H), 1.57 (d, 3H).

(3) 720 g of triphenylphosphine, 180 g of imidazole and 2.7 L of dichloromethane were added into a reaction bulb to obtain a mixture, and 700 g of iodine was added into the mixture in batches at −5° C. under the nitrogen protection. After the completion of the adding, the reactants were subjected to a first reaction at −5° C. for 30 min while stirring. Then 360 g of 4-fluoro-2-(1-hydroxyethyl)-1-nitrobenzene obtained in step (2) was added dropwise into the reaction system. After the completion of the dropwise adding, the reaction system was subjected to a second reaction at −5° C. for 3 h. Then the resulting reaction solution was sampled and measured with HPLC to determine whether the reaction reached the end point. After reaching the end point, 0.5 N of hydrochloric acid and ethyl acetate were added into the resulting reaction solution, and the resulting mixture was stirred, stood for a period time and separated liquid, obtaining an aqueous phase and an organic phases. The aqueous phase was extracted once with dichloromethane, and the organic phase was combined. The combined organic phase was washed with saturated salt solution, saturated sodium bicarbonate aqueous solution and saturated salt water in sequence, and then concentrated until no fraction came out, obtaining a mixture of 4-fluoro-2-(1-iodoethyl)-1-nitrobenzene and triphenylphosphine oxide, which could be directly used for the next step.

(4) The product obtained in step (3) was dissolved in 2.8 L of N,N-dimethylformamide and stirred to obtain a mixture, and 90 g of sodium borohydride was added into the mixture in batches at 25° C. The reactants were reacted at 25° C. for 3 h while stirring. Then the resulting reaction solution was sampled and measured with HPLC to determine whether the reaction reached the end point. After reaching the end point, 0.5 N of hydrochloric acid and isopropyl ether were added into the resulting reaction solution. The resulting mixture was stirred at 10° C. and filtered, obtaining a filter cake. The filter cake was washed with isopropyl ether, and the resulting filter liquor was combined, stirred, stood for a period and separated liquid, obtaining an aqueous phase and an organic phases. The aqueous phase was extracted three times with isopropyl ether, and the organic phase was combined and washed with saturated salt water, saturated sodium bicarbonate aqueous solution, 10% sodium thiosulfate aqueous solution and saturated salt water in sequence, and concentrated until no fraction came out. The residue was distilled under reduced pressure (Filler distillation column) to collect fractions at 64-66° C. and a pressure of 0.1 Torr, obtaining 200 g of target product 2-ethyl-4-fluoro-1-nitrobenzene. The yield was 60% and the purity was 98.9%.

The target product 2-ethyl-4-fluoro-1-nitrobenzene was tested, and the results were as follows: $^1$H-NMR (300 MHz, CDCl$_3$): δ 8.00 (m, 1H), 7.05 (m, 2H), 2.98 (q, 2H), 1.30 (t, 3H).

Example 2

The present example provided a method for preparing 2-ethyl-4-fluoro-1-nitrobenzene, which was performed according to the following procedure:

(1) 650 g of fuming nitric acid was added into a reaction bulb, and 100 g 3-fluoroacetophenone was added dropwise into the reaction bulb at −10° C. After the completion of the dropwise adding, the reactants were reacted at −10° C. for 3 h while stirring, obtaining a reaction solution. Then the reaction solution was sampled and measured with HPLC to determine whether the reaction reached the end point. After reaching the end point, the reaction solution was quenched by slowly pouring into ice water, stirred at 0° C. for 1 h and filtered, obtaining a solid phase. The solid phase was collected and washed with water, and then the washed solid phase was dried by vacuum, obtaining 105 g of 1-(5-fluoro-2-nitrophenyl)ethanone. The yield was 79% and the purity was 98.4%.

The product 1-(5-fluoro-2-nitrophenyl)ethanone was tested, and the results were as follows: $^1$H-NMR (300 MHz, CDCl$_3$): δ 8.25 (m, 1H), 7.25 (m, 1H), 7.10 (d, 1H), 2.57 (s, 3H).

(2) 105 g of 1-(5-fluoro-2-nitrophenyl)ethanone obtained in step (1), 0.5 L of tetrahydrofuran and 0.15 L of absolute methanol were added into a reaction bulb to obtain a mixture, and 22 g of sodium borohydride was added into the mixture in batches at 20° C. After the completion of the adding, the reactants were reacted at 23° C. for 2 h while stirring, obtaining a reaction solution. Then the reaction solution was sampled and measured with HPLC to determine whether the reaction reached the end point. After reaching the end point, 0.5 N of hydrochloric acid and ethyl acetate were added thereto, and the resulting mixture was stirred, stood for a period, and separated liquid, obtaining an aqueous phase and an organic phases. The organic phase was collected, and the aqueous phase was extracted twice with ethyl acetate. The organic phase was combined and washed with saturated salt solution, and concentrated until no fraction came out. Anhydrous sodium sulfate, activated carbon and dichloromethane were added into the concentrated product to obtain a mixture, and the mixture was stirred for 2 h and filtered, obtaining a filter cake. The filter cake was washed with dichloromethane, and the resulting filter liquor was combined, concentrated and replaced twice with dichloromethane, obtaining 102 g of 4-fluoro-2-(1-hydroxyethyl)-1-nitrobenzene. The yield was 96%, and the purity was 99.1%.

The product 4-fluoro-2-(1-hydroxyethyl)-1-nitrobenzene was tested, and the results were as follows: $^1$H-NMR (300 MHz, CDCl$_3$): δ 8.05 (m, 1H), 7.60 (dd, 1H), 7.11 (m, 1H), 5.52 (q, 1H), 2.35 (br, 1H), 1.57 (d, 3H).

(3) 102 g of 4-fluoro-2-(1-hydroxyethyl)-1-nitrobenzene obtained in step (2), 1 L of dichloromethane and 84 g of triethylamine were added into a reaction bulb to obtain a mixture, and 95 g of methanesulfonyl chloride was added dropwise into the mixture in batches at 5° C. After the completion of the dropwise adding, the reactants were reacted at 25° C. for 5 h while stirring, obtaining a reaction solution. Then 0.5 N of hydrochloric acid and dichloromethane were added thereto, and the resulting mixture was stirred, stood for a period time and separated liquid, obtaining an aqueous phase and an organic phases. The aqueous phase was extracted twice with dichloromethane, and the organic phase was combined and washed with saturated salt solution, saturated sodium bicarbonate aqueous solution and saturated salt solution in sequence, and concentrated until no fraction came out. Isopropyl ether was added into the concentrated product to pulp, obtaining a pulp suspension. The pulp suspension was filtered and dried by vacuum, obtaining 128 g of 1-(5-fluoro-2-nitrobenzene)ethylmethanesulfonate. The yield was 87%, and the purity was 95.3%.

The product 1-(5-fluoro-2-nitrobenzene)ethylmethanesulfonate was tested, and the results were as follows: $^1$H-NMR (300 MHz, CDCl$_3$): δ 8.16 (m, 1H), 7.52 (dd, 1H), 7.21 (m, 1H), 6.42 (t, 1H), 3.04 (s, 3H), 1.79 (d, 3H).

(4) 128 g of 1-(5-fluoro-2-nitrobenzene)ethylmethanesulfonate obtained in step (3), 109 g of sodium iodide and 1 L of acetone were added into a reaction bulb to obtain a mixture. The mixture was reacted at 35° C. for 10 h while stirring, obtaining a reactant. During the reaction, about 700 mL acetone was evaporated. Isopropyl ether and water were added thereto, and the reactant was stirred, stood for a period time and separated liquid, obtaining an aqueous phase and an organic phases. The aqueous phase was extracted once with isopropyl ether, and the organic phase was combined, and washed twice with saturated salt solution, and concentrated until no fraction came out, obtaining cude 4-fluoro-2-(1-iodoethyl)-1-nitrobenzene, which could be directly used for the next step.

(5) The product obtained in step (4) was dissolved in 0.7 L of N,N-dimethylformamide and stirred to obtain a mixture, and 22 g of sodium borohydride was added into the mixture in batches at 20° C. The reactants were reacted at 30° C. for 3 h while stirring. Then the resulting reaction solution was sampled and measured with HPLC to determine whether the reaction reached the end point. After reaching the end point, 0.5 N of hydrochloric acid and isopropyl ether were added into the resulting reaction solution. The resulting mixture was stirred at 15° C. and filtered, obtaining a filter cake. The filter cake was washed with isopropyl ether, and the resulting filter liquor was combined, stirred, stood for a period and separated liquid, obtaining an aqueous phase and an organic phases. The aqueous phase was extracted three times with isopropyl ether, and the organic phase was combined and washed with saturated salt water, saturated sodium bicarbonate aqueous solution, 10% sodium thiosulfate aqueous solution and saturated salt water in sequence, and concentrated until no fraction came out. The residue was distilled under reduced pressure (Filler distillation column) to collect fractions at 64-66° C. and a pressure of 0.1 Torr, obtaining 57 g of target product 2-ethyl-4-fluoro-1-nitrobenzene. The yield was 70% and the purity was 99.2%.

The target product 2-ethyl-4-fluoro-1-nitrobenzene was tested, and the results were as follows: $^1$H-NMR (300 MHz, CDCl$_3$): δ 8.00 (m, 1H), 7.05 (m, 2H), 2.98 (q, 2H), 1.30 (t, 3H).

Example 3

The present example provided a method for preparing 2-ethyl-4-fluoro-1-nitrobenzene, which was performed according to the following procedure:

(1) 1500 g of fuming nitric acid was added into a reaction bulb, and 300 g 3-fluoroacetophenone was added dropwise into the reaction bulb at −15° C. After the completion of the dropwise adding, the reactants were reacted at −15° C. for 5 h while stirring, obtaining a reaction solution. Then the reaction solution was sampled and measured with HPLC to determine whether the reaction reached the end point. After reaching the end point, the reaction solution was quenched by slowly pouring into ice water, stirred at 0° C. for 30 min and filtered, obtaining a solid phase. The solid phase was collected and washed with water, and then the washed solid phase was dried by vacuum, obtaining 310 g of 1-(5-fluoro-2-nitrophenyl)ethanone. The yield was 78% and the purity was 98.7%.

The product 1-(5-fluoro-2-nitrophenyl)ethanone was tested, and the results were as follows: $^1$H-NMR (300 MHz, CDCl$_3$): δ 8.25 (m, 1H), 7.25 (m, 1H), 7.10 (d, 1H), 2.57 (s, 3H).

(2) 310 g of 1-(5-fluoro-2-nitrophenyl)ethanone obtained in step (1), 1.1 L of tetrahydrofuran and 0.3 L of absolute methanol were added into a reaction bulb to obtain a mixture, and 19.5 g of sodium borohydride was added into the mixture in batches at 15° C. After the completion of the adding, the reactants were reacted at 15° C. for 3 h while stirring, obtaining a reaction solution. Then the reaction solution was sampled and measured with HPLC to determine whether the reaction reached the end point. After reaching the end point, 0.5 N of hydrochloric acid and ethyl acetate were added thereto, and the resulting mixture was stirred, stood for a period, and separated liquid, obtaining an aqueous phase and an organic phases. The organic phase was collected, and the aqueous phase was extracted twice with ethyl acetate. The organic phase was combined and washed with saturated salt solution, and concentrated until no fraction came out. Anhydrous sodium sulfate, activated carbon and dichloromethane were added into the concentrated product to obtain a mixture, and the mixture was stirred for 2 h and filtered, obtaining a filter cake. The filter cake was washed with dichloromethane, and the resulting filter liquor was combined, concentrated and replaced twice with dichloromethane, obtaining 307 g of 4-fluoro-2-(1-hydroxyethyl)-1-nitrobenzene. The yield was 98%, and the purity was 98.8%.

The product 4-fluoro-2-(1-hydroxyethyl)-1-nitrobenzene was tested, and the results were as follows: $^1$H-NMR (300 MHz, CDCl$_3$): δ 8.05 (m, 1H), 7.60 (dd, 1H), 7.11 (m, 1H), 5.52 (q, 1H), 2.35 (br, 1H), 1.57 (d, 3H).

(3) 567 g of triphenylphosphine, 147 g of imidazole and 1.8 L of dichloromethane were added into a reaction bulb to obtain a mixture, and 548 g of iodine was added into the mixture in batches at −5° C. under the nitrogen protection. After the completion of the adding, the reactants were subjected to a first reaction at −5° C. for 40 min while stirring. Then 307 g of 4-fluoro-2-(1-hydroxyethyl)-1-nitrobenzene obtained in step (2) was added dropwise into the reaction system. After the completion of the dropwise adding, the reaction system was subjected to a second reaction at −5° C. for 5 h. Then the resulting reaction solution was sampled and measured with HPLC to determine whether the reaction reached the end point. After reaching the end point, 0.5 N of hydrochloric acid and ethyl acetate were added into the resulting reaction solution, and the resulting mixture was stirred, stood for a period time and separated liquid, obtaining an aqueous phase and an organic phases. The aqueous phase was extracted once with dichloromethane, and the organic phase was combined. The combined organic phase was washed with saturated salt solution, saturated sodium bicarbonate aqueous solution and saturated salt water in sequence, and then concentrated until no fraction came out, obtaining a mixture of 4-fluoro-2-(1-iodoethyl)-1-nitrobenzene and triphenylphosphine oxide, which could be directly used for the next step.

(4) The product obtained in step (3) was dissolved in 1.7 L of N,N-dimethylformamide and stirred to obtain a mixture, and 67 g of sodium borohydride was added into the mixture in batches at 25° C. The reactants were reacted at 25° C. for 2 h while stirring. Then the resulting reaction solution was sampled and measured with HPLC to determine whether the reaction reached the end point. After reaching the end point, 0.5 N of hydrochloric acid and isopropyl ether were added into the resulting reaction solution. The resulting mixture was stirred at 10° C. and filtered, obtaining a filter cake. The filter cake was washed with isopropyl ether, and the resulting filter liquor was combined, stirred, stood for a period and separated liquid, obtaining an aqueous phase and an organic phases. The aqueous phase was extracted three times with isopropyl ether, and the organic phase was combined and washed with saturated salt water, saturated sodium bicarbonate aqueous solution, 10% sodium thiosulfate aqueous solution and saturated salt water in sequence, and concentrated until no fraction came out. The residue was distilled under reduced pressure (Filler distillation column) to collect fractions at 64-66° C. and a pressure of 0.1 Torr, obtaining 188 g of target product 2-ethyl-4-fluoro-1-nitrobenzene. The yield was 67% and the purity was 99.2%.

The target product 2-ethyl-4-fluoro-1-nitrobenzene was tested, and the results were as follows: $^1$H-NMR (300 MHz, CDCl$_3$): δ 8.00 (m, 1H), 7.05 (m, 2H), 2.98 (q, 2H), 1.30 (t, 3H)

Example 4

The present example provided a method for preparing 2-ethyl-4-fluoro-1-nitrobenzene, which was performed according to the following procedure:

(1) 2640 g of fuming nitric acid was added into a reaction bulb, and 330 g 3-fluoroacetophenone was added dropwise into the reaction bulb at −5° C. After the completion of the dropwise adding, the reactants were reacted at −5° C. for 5 h while stirring, obtaining a reaction solution. Then the reaction solution was sampled and measured with HPLC to determine whether the reaction reached the end point. After reaching the end point, the reaction solution was quenched by slowly pouring into ice water, stirred at 5° C. for 90 min and filtered, obtaining a solid phase. The solid phase was collected and washed with water, and then the washed solid phase was dried by vacuum, obtaining 354 g of 1-(5-fluoro-2-nitrophenyl)ethanone. The yield was 81% and the purity was 98.3%.

The product 1-(5-fluoro-2-nitrophenyl)ethanone was tested, and the results were as follows: $^1$H-NMR (300 MHz, CDCl$_3$): δ 8.25 (m, 1H), 7.25 (m, 1H), 7.10 (d, 1H), 2.57 (s, 3H).

(2) 354 g of 1-(5-fluoro-2-nitrophenyl)ethanone obtained in step (1), 2 L of tetrahydrofuran and 0.8 L of absolute methanol were added into a reaction bulb to obtain a mixture, and 145 g of sodium borohydride was added into the mixture in batches at 25° C. After the completion of the adding, the reactants were reacted at 25° C. for 1 h while stirring, obtaining a reaction solution. Then the reaction solution was sampled and measured with HPLC to determine whether the reaction reached the end point. After reaching the end point, 0.5 N of hydrochloric acid and ethyl acetate were added thereto, and the resulting mixture was stirred, stood for a period, and separated liquid, obtaining an aqueous phase and an organic phases. The organic phase was collected, and the aqueous phase was extracted twice with ethyl acetate. The organic phase was combined and washed with saturated salt solution, and concentrated until no fraction came out. Anhydrous sodium sulfate, activated carbon and dichloromethane were added into the concentrated product to obtain a mixture, and the mixture was stirred for 2 h and filtered, obtaining a filter cake. The filter cake was washed with dichloromethane, and the resulting filter liquor was combined, concentrated and replaced twice with dichloromethane, obtaining 340 g of 4-fluoro-2-(1-hydroxyethyl)-1-nitrobenzene. The yield was 95%, and the purity was 99.3%.

The product 4-fluoro-2-(1-hydroxyethyl)-1-nitrobenzene was tested, and the results were as follows: $^1$H-NMR (300 MHz, CDCl$_3$): δ 8.05 (m, 1H), 7.60 (dd, 1H), 7.11 (m, 1H), 5.52 (q, 1H), 2.35 (br, 1H), 1.57 (d, 3H).

1203 g of triphenylphosphine, 312 g of imidazole and 6.8 L of dichloromethane were added into a reaction bulb to obtain a mixture, and 1160 g of iodine was added into the mixture in batches at 0° C. under the nitrogen protection. After the completion of the adding, the reactants were subjected to a first reaction at −5° C. for 20 min while stirring. Then 340 g of 4-fluoro-2-(1-hydroxyethyl)-1-nitrobenzene obtained in step (2) was added dropwise into the reaction system. After the completion of the dropwise adding, the reaction system was subjected to a second reaction at 5° C. for 2 h. Then the resulting reaction solution was sampled and measured with HPLC to determine whether the reaction reached the end point. After reaching the end point, 0.5 N of hydrochloric acid and ethyl acetate were added into the resulting reaction solution, and the resulting mixture was stirred, stood for a period time and separated liquid, obtaining an aqueous phase and an organic phases. The aqueous phase was extracted once with dichloromethane, and the organic phase was combined. The combined organic phase was washed with saturated salt solution, saturated sodium bicarbonate aqueous solution and saturated salt water in sequence, and then concentrated until no fraction came out, obtaining a mixture of 4-fluoro-2-(1-iodoethyl)-1-nitrobenzene and triphenylphosphine oxide, which could be directly used for the next step.

(4) The product obtained in step (3) was dissolved in 3.6 L of N,N-dimethylformamide and stirred to obtain a mixture, and 104 g of sodium borohydride was added into the mixture in batches at 25° C. The reactants were reacted at 30° C. for 4 h while stirring. Then the resulting reaction solution was sampled and measured with HPLC to determine whether the reaction reached the end point. After reaching the end point, 0.5 N of hydrochloric acid and isopropyl ether were added into the resulting reaction solution. The resulting mixture was stirred at 15° C. and filtered, obtaining a filter cake. The filter cake was washed with isopropyl ether, and the resulting filter liquor was combined, stirred, stood for a period and separated liquid, obtaining an aqueous phase and an organic phases. The aqueous phase was extracted three times with isopropyl ether, and the organic phase was combined and washed with saturated salt water, saturated sodium bicarbonate aqueous solution, 10% sodium thiosulfate aqueous solution and saturated salt water in sequence, and concentrated until no fraction came out. The residue was distilled under reduced pressure (Filler distillation column) to collect fractions at 64-66° C. and a pressure of 0.1 Torr, obtaining 213.4 g of target product 2-ethyl-4-fluoro-1-nitrobenzene. The yield was 69% and the purity was 99.0%.

The target product 2-ethyl-4-fluoro-1-nitrobenzene was tested, and the results were as follows: $^1$H-NMR (300 MHz, CDCl$_3$): δ 8.00 (m, 1H), 7.05 (m, 2H), 2.98 (q, 2H), 1.30 (t, 3H).

Example 5

The present example provided a method for preparing 2-ethyl-4-fluoro-1-nitrobenzene, which was performed according to the following procedure:

(1) 700 g of fuming nitric acid was added into a reaction bulb, and 100 g 3-fluoroacetophenone was added dropwise into the reaction bulb at −10° C. After the completion of the dropwise adding, the reactants were reacted at −15° C. for 4 h while stirring, obtaining a reaction solution. Then the reaction solution was sampled and measured with HPLC to determine whether the reaction reached the end point. After reaching the end point, the reaction solution was quenched by slowly pouring into ice water, stirred at 5° C. for 40 min and filtered, obtaining a solid phase. The solid phase was collected and washed with water, and then the washed solid phase was dried by vacuum, obtaining 108 g of 1-(5-fluoro-2-nitrophenyl)ethanone. The yield was 81.2% and the purity was 98.6%.

The product 1-(5-fluoro-2-nitrophenyl)ethanone was tested, and the results were as follows: $^1$H-NMR (300 MHz, CDCl$_3$): δ 8.25 (m, 1H), 7.25 (m, 1H), 7.10 (d, 1H), 2.57 (s, 3H).

(2) 108 g of 1-(5-fluoro-2-nitrophenyl)ethanone obtained in step (1), 0.6 L of tetrahydrofuran and 0.2 L of absolute methanol were added into a reaction bulb to obtain a mixture, and 22.5 g of sodium borohydride was added into the mixture in batches at 20° C. After the completion of the adding, the reactants were reacted at 20° C. for 2.5 h while stirring, obtaining a reaction solution. Then the reaction solution was sampled and measured with HPLC to determine whether the reaction reached the end point. After reaching the end point, 0.4 N of hydrochloric acid and ethyl acetate were added thereto, and the resulting mixture was stirred, stood for a period, and separated liquid, obtaining an aqueous phase and an organic phases. The organic phase was collected, and the aqueous phase was extracted twice with ethyl acetate. The organic phase was combined and washed with saturated salt solution, and concentrated until no fraction came out. Anhydrous sodium sulfate, activated carbon and dichloromethane were added into the concentrated product to obtain a mixture, and the mixture was stirred for 1 h and filtered, obtaining a filter cake. The filter cake was washed with dichloromethane, and the resulting filter liquor was combined, concentrated and replaced twice with dichloromethane, obtaining 107 g of 4-fluoro-2-(1-hydroxyethyl)-1-nitrobenzene. The yield was 98%, and the purity was 99.0%.

The product 4-fluoro-2-(1-hydroxyethyl)-1-nitrobenzene was tested, and the results were as follows: $^1$H-NMR (300 MHz, CDCl$_3$): δ 8.05 (m, 1H), 7.60 (dd, 1H), 7.11 (m, 1H), 5.52 (q, 1H), 2.35 (br, 1H), 1.57 (d, 3H).

(3) 107 g of 4-fluoro-2-(1-hydroxyethyl)-1-nitrobenzene obtained in step (2), 0.9 L of dichloromethane and 61.5 g of triethylamine were added into a reaction bulb to obtain a mixture, and 70 g of methanesulfonyl chloride was added dropwise into the mixture in batches at 0° C. After the completion of the dropwise adding, the reactants were reacted at 20° C. for 6 h while stirring, obtaining a reaction solution. Then 0.5 N of hydrochloric acid and dichloromethane were added thereto, and the resulting mixture was stirred, stood for a period time and separated liquid, obtaining an aqueous phase and an organic phases. The aqueous phase was extracted twice with dichloromethane, and the organic phase was combined and washed with saturated salt solution, saturated sodium bicarbonate aqueous solution and saturated salt solution in sequence, and concentrated until no fraction came out. Isopropyl ether was added into the concentrated product to pulp, obtaining a pulp suspension. The pulp suspension was filtered and dried by vacuum, obtaining 126.2 g of 1-(5-fluoro-2-nitrobenzene)ethylmethanesulfonate. The yield was 83%, and the purity was 94.9%.

The product 1-(5-fluoro-2-nitrobenzene)ethylmethanesulfonate was tested, and the results were as follows: $^1$H-NMR (300 MHz, CDCl$_3$): δ 8.16 (m, 1H), 7.52 (dd, 1H), 7.21 (m, 1H), 6.42 (t, 1H), 3.04 (s, 3H), 1.79 (d, 3H).

(4) 126.2 g of 1-(5-fluoro-2-nitrobenzene)ethylmethanesulfonate obtained in step (3), 72 g of sodium iodide and 0.9 L of acetone were added into a reaction bulb to obtain a mixture. The mixture was reacted at 40° C. for 6 h while stirring, obtaining a reactant. During the reaction, about 650 mL acetone was evaporated. Isopropyl ether and water were added thereto, and the reactant was stirred, stood for a period time and separated liquid, obtaining an aqueous phase and an organic phases. The aqueous phase was extracted once with isopropyl ether, and the organic phase was combined, and washed twice with saturated salt solution, and concentrated until no fraction came out, obtaining cude 4-fluoro-2-(1-iodoethyl)-1-nitrobenzene, which could be directly used for the next step.

(5) The product obtained in step (4) was dissolved in 0.95 L of N,N-dimethylformamide and stirred to obtain a mixture, and 22.5 g of sodium borohydride was added into the mixture in batches at 20° C. The reactants were reacted at 25° C. for 4 h while stirring. Then the resulting reaction solution was sampled and measured with HPLC to determine whether the reaction reached the end point. After reaching the end point, 0.5 N of hydrochloric acid and isopropyl ether were added into the resulting reaction solution. The resulting mixture was stirred at 10° C. and filtered, obtaining a filter cake. The filter cake was washed with isopropyl ether, and the resulting filter liquor was combined, stirred, stood for a period and separated liquid, obtaining an aqueous phase and an organic phases. The aqueous phase was extracted three times with isopropyl ether, and the organic phase was combined and washed with saturated salt water, saturated sodium bicarbonate aqueous solution, 10% sodium thiosulfate aqueous solution and saturated salt water in sequence, and concentrated until no fraction came out. The residue was distilled under reduced pressure (Filler distillation column) to collect fractions at 64-66° C. and a pressure of 0.1 Torr, obtaining 60 g of target product 2-ethyl-4-fluoro-1-nitrobenzene. The yield was 75% and the purity was 98.9%.

The target product 2-ethyl-4-fluoro-1-nitrobenzene was tested, and the results were as follows: $^1$H-NMR (300 MHz, CDCl$_3$): δ 8.00 (m, 1H), 7.05 (m, 2H), 2.98 (q, 2H), 1.30 (t, 3H).

Example 6

The present example provided a method for preparing 2-ethyl-4-fluoro-1-nitrobenzene, which was performed according to the following procedure:

(1) 650 g of fuming nitric acid was added into a reaction bulb, and 100 g 3-fluoroacetophenone was added dropwise into the reaction bulb at −10° C. After the completion of the dropwise adding, the reactants were reacted at −10° C. for 3 h while stirring, obtaining a reaction solution. Then the reaction solution was sampled and measured with HPLC to determine whether the reaction reached the end point. After reaching the end point, the reaction solution was quenched by slowly pouring into ice water, stirred at 0° C. for 1 h and filtered, obtaining a solid phase. The solid phase was collected and washed with water, and then the washed solid phase was dried by vacuum, obtaining 99.5 g of 1-(5-fluoro-2-nitrophenyl)ethanone. The yield was 75% and the purity was 98.2%.

The product 1-(5-fluoro-2-nitrophenyl)ethanone was tested, and the results were as follows: $^1$H-NMR (300 MHz, CDCl$_3$): δ 8.25 (m, 1H), 7.25 (m, 1H), 7.10 (d, 1H), 2.57 (s, 3H).

(2) 99.5 g of 1-(5-fluoro-2-nitrophenyl)ethanone obtained in step (1), 0.5 L of tetrahydrofuran and 0.15 L of absolute methanol were added into a reaction bulb to obtain a mixture, and 21 g of sodium borohydride was added into the mixture in batches at 20° C. After the completion of the adding, the reactants were reacted at 25° C. for 3 h while stirring, obtaining a reaction solution. Then the reaction solution was sampled and measured with HPLC to determine whether the reaction reached the end point. After reaching the end point, 0.5 N of hydrochloric acid and ethyl acetate were added thereto, and the resulting mixture was stirred, stood for a period, and separated liquid, obtaining an aqueous phase and an organic phases. The organic phase was collected, and the aqueous phase was extracted twice with ethyl acetate. The organic phase was combined and washed with saturated salt solution, and concentrated until no fraction came out. Anhydrous sodium sulfate, activated carbon and dichloromethane were added into the concentrated product to obtain a mixture, and the mixture was stirred for 2 h and filtered, obtaining a filter cake. The filter cake was washed with dichloromethane, and the resulting filter liquor was combined, concentrated and replaced twice with dichloromethane, obtaining 100.5 g of 4-fluoro-2-(1-hydroxyethyl)-1-nitrobenzene. The yield was 99%, and the purity was 98.6%.

The product 4-fluoro-2-(1-hydroxyethyl)-1-nitrobenzene was tested, and the results were as follows: $^1$H-NMR (300 MHz, CDCl$_3$): δ 8.05 (m, 1H), 7.60 (dd, 1H), 7.11 (m, 1H), 5.52 (q, 1H), 2.35 (br, 1H), 1.57 (d, 3H).

(3) 100.5 g of 4-fluoro-2-(1-hydroxyethyl)-1-nitrobenzene obtained in step (2), 1.35 L of dichloromethane and 109 g of triethylamine were added into a reaction bulb to obtain a mixture, and 124 g of methanesulfonyl chloride was added dropwise into the mixture in batches at 10° C. After the completion of the dropwise adding, the reactants were reacted at 30° C. for 4 h while stirring, obtaining a reaction solution. Then 0.5 N of hydrochloric acid and dichloromethane were added thereto, and the resulting mixture was stirred, stood for a period time and separated liquid, obtaining an aqueous phase and an organic phases. The aqueous phase was extracted twice with dichloromethane, and the organic phase was combined and washed with saturated salt solution, saturated sodium bicarbonate aqueous solution and saturated salt solution in sequence, and concentrated until no fraction came out. Isopropyl ether was added into the concentrated product to pulp, obtaining a pulp suspension. The pulp suspension was filtered and dried by vacuum, obtaining 121.3 g of 1-(5-fluoro-2-nitrobenzene)ethylmethanesulfonate. The yield was 85%, and the purity was 93.9%.

The product 1-(5-fluoro-2-nitrobenzene)ethylmethanesulfonate was tested, and the results were as follows: $^1$H-NMR (300 MHz, CDCl$_3$): δ 8.16 (m, 1H), 7.52 (dd, 1H), 7.21 (m, 1H), 6.42 (t, 1H), 3.04 (s, 3H), 1.79 (d, 3H).

(4) 121.3 g of 1-(5-fluoro-2-nitrobenzene)ethylmethanesulfonate obtained in step (3), 207 g of sodium iodide and 1.1 L of acetone were added into a reaction bulb to obtain a mixture. The mixture was reacted at 35° C. for 16 h while stirring, obtaining a reactant. During the reaction, about 800 mL acetone was evaporated. Isopropyl ether and water were added thereto, and the reactant was stirred, stood for a period time and separated liquid, obtaining an aqueous phase and an organic phases. The aqueous phase was extracted once with isopropyl ether, and the organic phase was combined and washed twice with saturated salt solution, and concentrated until no fraction came out, obtaining cude 4-fluoro-2-(1-iodoethyl)-1-nitrobenzene, which could be directly used for the next step.

(5) The product obtained in step (4) was dissolved in 0.7 L of N,N-dimethylformamide and stirred to obtain a mixture, and 22.6 g of sodium borohydride was added into the mixture in batches at 20° C. The reactants were reacted at 25° C. for 4 h while stirring. Then the resulting reaction solution was sampled and measured with HPLC to determine whether the reaction reached the end point. After reaching the end point, 0.5 N of hydrochloric acid and isopropyl ether were added into the resulting reaction solution. The resulting mixture was stirred at 10° C. and filtered, obtaining a filter cake. The filter cake was washed with isopropyl ether, and the resulting filter liquor was combined, stirred, stood for a period and separated liquid, obtaining an aqueous phase and an organic phases. The aqueous phase was extracted three times with isopropyl ether, and the organic phase was combined and washed with saturated salt water, saturated sodium bicarbonate aqueous solution, 10% sodium thiosulfate aqueous solution and saturated salt water in sequence, and concentrated until no fraction came out. The residue was distilled under reduced pressure (Filler distillation column) to collect fractions at 64-66° C. and a pressure of 0.1 Torr, obtaining 60 g of target product 2-ethyl-4-fluoro-1-nitrobenzene. The yield was 77% and the purity was 98.5%.

The target product 2-ethyl-4-fluoro-1-nitrobenzene was tested, and the results were as follows: $^1$H-NMR (300 MHz, CDCl$_3$): δ 8.00 (m, 1H), 7.05 (m, 2H), 2.98 (q, 2H), 1.30 (t, 3H).

The applicant declares that in the present disclosure, the method for preparing 2-ethyl-4-fluoro-1-nitrobenzene according to the present disclosure is illustrated by the above examples, but the present disclosure will not be limited to the above examples, that is, it does not mean that the present disclosure must rely on the above examples for implementation. The skilled in the art shall understand that any improvements to the present disclosure, such as the equivalent replacement of the raw materials, the addition of auxiliary components, the selection of specific ways and the like fall within the scope of protection and disclosure of the present disclosure.

What is claimed is:

1. A method for preparing 2-ethyl-4-fluoro-1-nitrobenzene, comprising,
   (1) nitrifying 3-fluoroacetophenone with a nitration reagent, to obtain 1-(5-fluoro-2-nitrophenyl)ethanone;
   (2) reducing 1-(5-fluoro-2-nitrophenyl)ethanone obtained in step (1) with a reducing agent, to obtain 4-fluoro-2-(1-hydroxyethyl)-1-nitrobenzene;
   (3) iodinating 4-fluoro-2-(1-hydroxyethyl)-1-nitrobenzene obtained in step (2), to obtain 4-fluoro-2-(1-iodoethyl)-1-nitrobenzene; and (4) reducing 4-fluoro-2-(1-iodoethyl)-1-nitrobenzene obtained in step (3) with a reducing agent, to obtain 2-ethyl-4-fluoro-1-nitrobenzene;

wherein the reaction route of the method is shown in Formula 1:

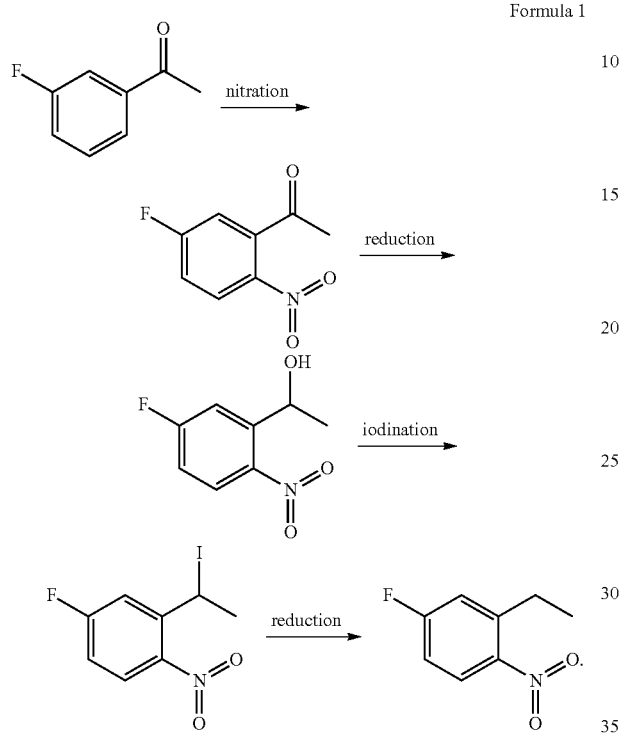

2. The method as claimed in claim 1, wherein the nitration reagent in step (1) is fuming nitric acid, and a mass ratio of the fuming nitric acid to 3-fluoroacetophenone is in the range of (5.0-8.0): 1.

3. The method as claimed in claim 1 or 2, wherein the nitrifying in step (1) is performed at a temperature of −15° C. to −5° C. for 2-5 h.

4. The method as claimed in claim 1, wherein step (1) further comprises subjecting a nitrified solution obtained after nitrifying 3-fluoroacetophenone to a post-treatment;

the post-treatment comprises: quenching the nitrified solution with ice water, stirring and filtering the nitrified solution, to obtain a solid phase, and collecting the solid phase, to obtain 1-(5-fluoro-2-nitrophenyl)ethanone, wherein the stirring is performed at a temperature of 0° C. to 5° C. for 30-90 min.

5. The method as claimed in claim 1, wherein the reducing agent used in step (2) is sodium borohydride, and a molar ratio of sodium borohydride to 1-(5-fluoro-2-nitrophenyl)ethanone is in the range of (0.3-2.0): 1.

6. The method as claimed in claim 1, wherein the reducing in step (2) is performed at a temperature of 15° C. to 25° C. for 1-3 h.

7. The method as claimed in claim 1, wherein the reducing in step (2) is performed in the presence of a solvent;

the solvent is tetrahydrofuran and/or absolute methanol, and the solvent is used in an amount of 0.8-1.5 L, based on 1 mol of 1-(5-fluoro-2-nitrophenyl)ethanone.

8. The method as claimed in claim 1, wherein step (2) further comprises subjecting a reduced solution obtained after reducing 1-(5-fluoro-2-nitrophenyl)ethanone to a post-treatment;

the post-treatment comprises: quenching the reduced solution with an acid, then extracting the reduced solution with a solvent to obtain an organic phase, and collecting the organic phase, then concentrating and purifying the organic phase, to obtain 4-fluoro-2-(1-hydroxyethyl)-1-nitrobenzene.

9. The method as claimed in claim 8, wherein the acid is hydrochloric acid with a concentration of 0.4-1 N, and the solvent used in the extracting is ethyl acetate.

10. The method as claimed in claim 1, wherein the iodinating in step (3) is performed by the following iodination scheme I or iodination scheme II, wherein, the iodination scheme I comprises: mixing triphenylphosphine and imidazole to obtain a mixture, then adding an iodine source into the mixture under a protective atmosphere, and subjecting the reactants to a first reaction, to obtain a reaction system; then adding 4-fluoro-2-(1-hydroxyethyl)-1-nitrobenzene into the reaction system, and subjecting the resulting mixture to a second reaction, to obtain 4-fluoro-2-(1-iodoethyl)-1-nitrobenzene; and the iodination scheme II comprises: adding methanesulfonyl chloride into 4-fluoro-2-(1-hydroxyethyl)-1-nitrobenzene to obtain a mixture, and subjecting the mixture to a methylsulfonylation reaction, to obtain 1-(5-fluoro-2-nitrobenzene)ethylmethanesulfonate;

then iodinating 1-(5-fluoro-2-nitrobenzene)ethylmethanesulfonate with an iodine source, to obtain 4-fluoro-2-(1-iodoethyl)-1-nitrobenzene;

wherein the reaction route is shown in Formula 2:

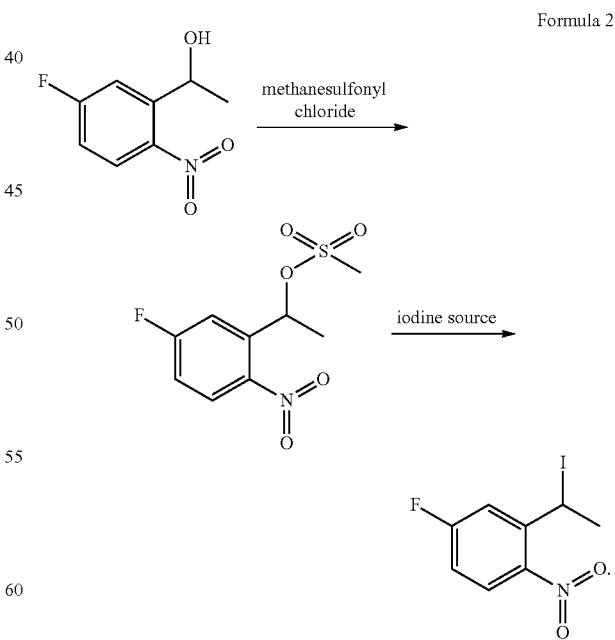

11. The method as claimed in claim 10, wherein the iodine source in the iodination scheme I is iodine;

a molar ratio of iodine, triphenylphosphine and imidazole is in the range of (0.95-1.05) : (0.95-1.05) : 1;

a molar ratio of iodine to 4-fluoro-2-(1-hydroxyethyl)-1-nitrobenzene is in the range of (1.3-2.5): 1.

12. The method as claimed in claim 10, wherein the reaction in the iodination scheme II is performed in the presence of a solvent, and the solvent is dichloromethane; the solvent is used in an amount of 0.8-1.5 L, based on 1 mol of triphenylphosphine.

13. The method as claimed in claim 10, wherein the first reaction in the iodination scheme I is performed at a temperature of −5° C. to 0° C. for 20-40 min, and
the second reaction in the iodination scheme I is performed at a temperature of −5° C. to 5° C. for 2-5 h.

14. The method as claimed in claim 10, wherein the iodination scheme I further comprises subjecting a reaction solution obtained after the second reaction to a post-treatment;
the post-treatment comprises: quenching the reaction solution with an acid, then seperating liquid to obtain an organic phase, and collecting the organic phase, then purifying and concentrating the organic phase, to obtain 4-fluoro-2-(1-iodoethyl)-1-nitrobenzene.

15. The method as claimed in claim 10, wherein a molar ratio of 4-fluoro-2-(1-hydroxyethyl)-1-nitrobenzene to methanesulfonyl chloride in the iodination scheme II is in the range of 1 : (1.05-2.0);
methanesulfonyl chloride added into 4-fluoro-2-(1-hydroxyethyl)-1-nitrobenzene by dropwise adding;
the dropwise adding is performed at a temperature of 0° C. to 10° C.;
raw materials for the methylsulfonylation reaction in the iodination scheme II further comprise an acid-binding agent;
the acid-binding agent is one selected from the group consisting of triethylamine, pyridine, sodium carbonate and sodium bicarbonate;
a molar ratio of the acid-binding agent to methanesulfonyl chloride is in the range of (0.9-1.1): 1;
the methylsulfonylation reaction in the iodination scheme II is performed in the presence of a solvent;
the solvent is dichloromethane;
the solvent is used in an amount of 1.5-2.5 L, based on 1 mol of 4-fluoro-2-(1-hydroxyethyl)-1-nitrobenzene;
the methylsulfonylation reaction in the iodination scheme II is performed at a temperature of 20° C. to 30° C. for 4-6 h.

16. The method as claimed in claim 10, wherein the iodination scheme II further comprises subjecting a reaction solution obtained after the methylsulfonylation reaction to a post-treatment;
the post-treatment comprises the following steps: quenching the reaction solution with an acid, then extracting the reaction solution to obtain an organic phase, and collecting the organic phase, then washing, concentrating and drying the organic phase, to obtain 1-(5-fluoro-2-nitrobenzene)ethylmethanesulfonate.

17. The method as claimed in claim 10, wherein the iodine source in the iodination scheme II is sodium iodide;
a molar ratio of sodium iodide to 1-(5-fluoro-2-nitrobenzene)ethylmethanesulfonate in the iodination scheme II is in the range of (1.0-3.0): 1;
the iodinating in the iodination scheme II is performed in the presence of a solvent; the solvent is acetone;
the solvent is used in an amount of 1.8-2.5 L, based on 1 mol of 1-(5-fluoro-2-nitrobenzene)ethylmethanesulfonate;
the iodinating in the iodination scheme II is performed at a temperature of 35° C. to 40° C. for 6-16 h.

18. The method as claimed in claim 1, wherein the reducing agent in step (4) is sodium borohydride;
a molar ratio of sodium borohydride to 4-fluoro-2-(1-iodoethyl)-1-nitrobenzene is in the range of (1.05-1.5): 1;
the reducing in step (4) is performed in the presence of a solvent; the solvent is N,N-dimethylformamide;
the solvent is used in an amount of 1-2 L, based on 1 mol of 4-fluoro-2-(1-iodoethyl)-1-nitrobenzene;
the reducing in step (4) is performed at a temperature of 25° C. to 30° C. for 2-4 h.

19. The method as claimed in claim 1, wherein step (4) further comprises subjecting a reduced solution obtained after reducing 4-fluoro-2-(1-iodoethyl)-1-nitrobenzene to a post-treatment;
the post-treatment comprises: quenching the reduced solution with an acid, then extracting the reduction solution with an organic solvent, and washing, concentrating and rectifying the extracted product, to obtain 2-ethyl-4-fluoro-1-nitrobenzene;
the organic solvent is isopropyl ether;
fractions produced during the rectifying is collected at a temperature of 64° C. to 66° C. and a pressure of 0.1 Ton.

20. The method as claimed in claim 1, wherein the method comprises:
(1) dropwise adding 3-fluoroacetophenone into fuming nitric acid at a temperature of -15° C. to -5° C.; after the completion of the dropwise adding, nitrating the reactants at a temperature of −15° C. to −5° C. for 2-5 h to obtain a nitrated solution; quenching the nitrated solution with ice water, stirring at a temperature of 0-5° C. for 30-90 min and filtering the nitrated solution to obtain a solid phase, and collecting the solid phase, to obtain 1-(5-fluoro-2-nitrophenyl)ethanone, wherein a mass ratio of fuming nitric acid to 3-fluoroacetophenone is in the range of (5.0-8.0) : 1;
(2) mixing 1-(5-fluoro-2-nitrophenyl)ethanone obtained in step (1) with a solvent to obtain a mixture, then adding sodium borohydride into the mixture, reducing the reactant at a temperature of 15-25° C. for 1-3 h to obtain a reduced solution, quenching the reduced solution with an acid, then extracting the reduced solution to obtain an organic phase, and collecting the organic phase, then concentrating and purifying the organic phase, to obtain 4-fluoro-2-(1-hydroxyethyl)-1-nitrobenzene, wherein a molar ratio of sodium borohydride to 1-(5-fluoro-2-nitrophenyl)ethanone is in the range of (0.3-2.0): 1;
(3) iodating 4-fluoro-2-(1-hydroxyethyl)-1-nitrobenzene obtained in step (2), wherein the iodating is performed by the following iodination scheme I or iodination scheme II, wherein
the iodination scheme I comprises: mixing triphenylphosphine, imidazole and a solvent to obtain a mixture, then adding iodine into the mixture at a temperature of −5-0° C. under a protective atmosphere, after the completion of the adding, reacting the reactants at a temperature of −5-0° C. for 20-40 min to obtain a reaction system, then dropwise adding 4-fluoro-2-(1-hydroxyethyl)-1-nitrobenzene into the reaction system, after the completion of the dropwise adding, reacting the resulting mixture at a temperature of −5-5° C. for 2-5 h to obtain a reaction solution, quenching the reaction solution with an acid, then seperating liquid to obtain an organic phase, and collecting the organic phase, then purifying and concentrating the organic phase, to obtain 4-fluoro- 2-(1-iodoethyl)-1-nitrobenzene, whierein a molar ratio of iodine, triphenylphosphine and imidazole is in the range of (0.95-1.05) : (0.95-1.05): 1, and a molar ratio of iodine to 4-fluoro-2-(1-hydroxyethyl)-1-nitrobenzene is in the range of (1.3-2.5): 1; and the iodination scheme II comprises: mixing 4-fluoro-2-(1-hydroxyethyl)-1-nitrobenzene, an acid-binding agent and a solvent to obtain a mixture, then dropwise adding methanesulfonyl chloride into the mixture at a temperature of 0-10° C., after the completion of the dropwise adding, subjecting the reactants to a methylsulfonylation reaction at a temperature of 20-30° C. for 4-6 h to obtain a reaction solution, quenching the reaction solution with an acid, then extracting the reaction solution, to obtain 1-(5-fluoro-2-nitrobenzene) ethylmethanesulfonate; iodating 1-(5-fluoro-2-nitrobenzene)ethylmethanesulfonate with sodium iodide in a solvent at a temperature of 35-40° C. for 6-16 h, then collecting, extracting and washing the resulting reaction solution, to obtain 4-fluoro-2-(1-iodoethyl)-1-nitrobenzene, wherein a molar ratio of 4-fluoro-2-(1-hydroxyethyl)-1-nitrobenzene to methanesulfonyl chloride is in the range of 1: (1.05-2.0), and a molar ratio of sodium iodide to 1-(5-fluoro-2-nitrobenzene) ethylmethanesulfonate is in the range of (1.0-3.0) : 1, and (4) mixing 4-fluoro-2-(1-iodoethyl)-1-nitrobenzene obtained in step (3) with a solvent to obtain a mixture, then adding sodium borohydride into the mixture, reducing the reactant at a temperature of 25-30° C. for 2-4 h to obtain a reduced solution, quenching the reduced solution with an acid, then purifying the reduced solution with a organic solvent, and washing, concentrating and rectifying the purified reduced solution to give fractions, then collecting the fractions at a temperature of 64-66° C. and a pressure of 0.1 Torr, to obtain 2-ethyl-4-fluoro-1-nitrobenzene, wherein a molar ratio of sodium borohydride to 4-fluoro-2-(1-iodoethyl)-1-nitrobenzene is in the range of (1.05-1.5): 1.

* * * * *